United States Patent [19]

Simmons et al.

[11] Patent Number: 5,807,684
[45] Date of Patent: Sep. 15, 1998

[54] MASTITIS TEST

[76] Inventors: Maxine Helen Simmons, 113 Amreins Road, Taupaki, Auckland 1009; Rosemary Katherine Cameron Sharpin, 74 Arney Road, Remuera, Auckland 1005, both of New Zealand

[21] Appl. No.: 669,420
[22] PCT Filed: Jan. 24, 1994
[86] PCT No.: PCT/NZ94/00003
 § 371 Date: Jul. 9, 1996
 § 102(e) Date: Jul. 9, 1996
[87] PCT Pub. No.: WO95/20159
 PCT Pub. Date: Jul. 27, 1995
[51] Int. Cl.$^6$ .................................................. G01N 33/53
[52] U.S. Cl. ........................................ 435/7.1; 435/7.92
[58] Field of Search ................................. 435/7.1, 7.92, 435/7.95

[56] References Cited

PUBLICATIONS

Anderson, KL et al. Amer. J. Vet. Research. 47(11):2405–2410, Nov. 1986.
Uhaa, IJ et al. Vet. Research Comm. 14:279–285, 1990.
Mackie, DP et al. Research in Vet. Sci. 40: 183–188, Mar. 1986.
Roitt, IM et al. in Immunology. Roitt, IM et al editors. Gower Medical Publ., London. pp. 25.1–25.10, 1985.

*Primary Examiner*—David Saunders
*Assistant Examiner*—F. Pierre VanderVegt
*Attorney, Agent, or Firm*—Young & Thompson

[57] ABSTRACT

A method of testing for the existence of mastitis in milk from cows either from an individual cow or from a herd of cows, by (a) obtaining a sample of milk to be tested, (b) determining whether immunoglobulin G2 ($IgG_2$) is present in said sample at a level above or below a predetermined level which is typically about 0.05 mg $IgG_2$ per milliliter of milk, by an ELISA comparison with immunoglobulin standards, and (c) classifying the individual cow or herd of cows as mastitis affected if said immunoglobulin is present in said sample at or above said predetermined level.

2 Claims, No Drawings

MASTITIS TEST

TECHNICAL FIELD OF THE INVENTION

This invention relates to methods of testing for mastitis in mammals including but not limited to humans, and for example it may be used in testing for the presence or absence of mastitis in dairy cows, either in single cows or bulk samples taken from numbers of animals.

BACKGROUND OF THE INVENTION

Mastitis is a disease of the breast, mammary gland or udder which is generally caused by infective micro-organisms. Mastitis is of inevitable widespread occurrence, since the mammae are glands intended to produce a rich food(intended for the young)at a warm temperature. Consequently micro-organisms may easily develop in such a medium and invade the body tissue as well, despite the presence of natural defense mechanisms.

The incidence of mastitis in cows within the dairy industry may be very high in some farms, and if chronic mastitis and carrier cows are included in the count it is relatively uncommon to find an incidence of less than 5% in a herd.

Testing may be carried out on samples of milk from individual cows or on bulk milk from a herd of cows. There is a need for a reliable test that may be used on milk, for example within a dairy factory, to indicate whether the general level of infection of a cow (individual samples) or within a herd (i.e., the testing of bulk milk) is acceptable. This process thus may become a significant step in quality assurance within the dairy industry.

Human intervention with milking machinery and the like is not the sole cause of mastitis, for an incidence of 5% has been recently described as typical of sheep on pasture—where generally one half of the udder is affected and the ewe cannot then raise twin lambs. Other mammals including humans may also be affected with mastitis.

Sub-acute or chronic mastitis may exist in the absence of clearly visible clinical signs and even the milk may appear to be grossly normal. In such cases one would discover that the micro-organisms tend to colonise the milk ducts and cisternae rather than the parenchyma where acute infections occur. It is extremely useful to locate, treat, and confirm as "cured" cows (or other dairy animals) having subacute mastitis for such animals carry the disease and release pathogenic microorganisms into the environment and particularly into milking machinery, from where they may infect others of the herd or flock.

A number of test methods have been developed, particularly with samples of milk, for use either at the side of the animal or within a laboratory on either individual or bulk samples, to detect subclinical mastitis. A variety of test methods are known which detect the cause of the disease directly, or which detect aspects of the usual response by the mammal to infection.

Examples of such milk-based tests are: evaluation of salt content or of leucocyte numbers (by manual or automated microscopic means or by using the viscosity developed after addition of detergent (eg, the well-known California test)), or by culture of micro-organisms (likely to return false negative results if antibiotics are present in the milk). There are also a number of specific tests to detect particular, predicted organisms generally by means of antibodies produced within the infected mammal, but specific tests are not useful if the microorganism is not known.

OBJECT OF THE INVENTION

It is an object of the invention to provide a method of testing for mastitis which at least provides the public with a useful choice.

SUMMARY OF INVENTION

Accordingly in one aspect the invention may broadly be said to consist of a method of testing for the occurrence of mastitis in mammals comprising the steps of:
(a) obtaining at least one sample of milk from at least one mammal to be tested;
(b) determining whether an immunoglobulin is present in said sample at a level above or below a predetermined level; and
(c) classifying said mammal or group of mammals as mastitis affected if said immunoglobulin is present in said sample at or above said pre-determined level.

In a second aspect the invention may broadly be said to consist of a method of testing for the occurrence of mastitis in groups of mammals comprising the steps of:
(a) obtaining a sample of bulk milk from at least one group of mammals to be tested;
(b) determining whether an immunoglobulin is present in said sample at a level above or below a predetermined level; and
(c) classifying said group of mammals as mastitis affected if said immunoglobulin is present in said sample at greater than said predetermined level.

Preferably said immunoglobulin is immunoglobulin $G2(IgG_2)$.

Preferably said predetermined level is about 0.05 mg $IgG_2$ per ml of milk.

Preferably said determination of the level of immunoglobulin is preferably carried out by the Enzyme Linked Immuno-Sorbent Assay (ELISA) comparison with immunoglobulin standards.

Alternatively said determination is carried out by single radial immunodiffusion comparison with immunoglobulin standards.

Alternatively said determination is preferably carried out by Dot Blot comparison with standard concentrations of said immunoglobulin.

Alternatively said determination is preferably carried out by another suitable comparative method for the measurement of $IgG_2$ In a further aspect the invention may be said to consist of a set of materials with which to perform one or more of the methods for testing for mastitis according to the principles disclosed in this specification.

DESCRIPTION OF THE PREFERRED EMBODIMENTS

The invention consists of the foregoing and also envisages constructions of which the following preferred embodiments are simply illustrative examples. Furthermore, it should be noted that while these examples are described in terms of determination of the level of bovine $IgG_2$ in milk samples taken from dairy cows, the method according to this invention can of course be applied to other dairy animals such as sheep and goats, or to other domestic animals (mammals), or to humans; in all of which cases a species-specific antigen will be used, as will be obvious to those skilled in the art to which the invention relates. This invention is in no way limited in its application to cows.

This invention may be said to be one of the class of tests for mastitis that are based on the measurement of a defense-mechanism substance produced by the affected mammal in response to an infection.

Example 1: Determination of $IgG_2$ in Bovine Milk Quarter Samples or Bulk Milk by Single Radial Immuno - Diffusion (RID)

RID Plate Manufacture

The following quantities are used in the manufacture of one plate.

Add 0.1 g agarose to 9.09 ml barbitone buffer (0.015 M barbitone 0.075 M sodium barbitone 0.1% sodium azide pH 8.6) and dissolve the agarose, by bringing the solution to a boil. After boiling, the solution is allowed to cool before 0.6 ml of 50% (w/v) polyethylene glycol 6000 is added. The temperature of the agarose is then stabilized at 56° C. in a waterbath before the addition of 300 μl of Goat Anti-Bovine $IgG_2$ antisera and 11 μl of blue dye, such as "Coomassie Blue" or other suitable dyes, which have the effect of making the precipitate more apparent.

The mixed solution is poured into a flat levelled plastic RID plate and is spread into the corners and sides of the plate. The agarose is allowed to harden then punched with 25 evenly spaced 4 mm diameter wells which are cleared by suction. Plates are then covered with their lids, sealed into foil bags and stored at 4° C. for later use.

Test Procedure

Bovine $IgG_2$ standards (prepared by weighing out pure freeze dried Bovine $IgG_2$ and dissolving in 0.15 M NaCl with 0.1% sodium azide) are pipetted into wells of an RID plate. 15 μl of each standard at concentrations of 005 mg/ml, 0.1 mg/ml, 0.25 mg/ml, and 0.5 mg/ml are pipetted into wells of the RID plate. The lower standards are preferably prepared by serial dilutions of the strongest concentration of standard.

Samples of milk are taken by any conventional method from cows to be tested and 15 μl of each sample to be tested is then pipetted into remaining wells of the RID plate.

The plate is covered and allowed to remain undisturbed on a horizontal surface for 24–36 hours. The diameters of the resulting precipitin zones are determined or "read" with a McSwiney ruler. A standard curve is constructed by graphing the zone diameters (mm) of each of the four standards on the y-axis against the $IgG_2$ concentration (mg/ml) on the x-axis. $IgG_2$, concentrations in the quarter samples are read off the standard curve.

An $IgG_2$ concentration in bulk milk in excess of 0.05 mg/ml is considered indicative of mastitis, and the mammal from which the particular sample was taken is classified according to this invention as mastitis affected.

Example 2: Determination of $IgG_2$ in Bovine Milk Quarter Samples or Bulk Milk by Enzyme Linked Immuno-Sorbent Assay (ELISA)

NB: Example 4 (vide infra) is a second preferred ELISA method.

Preparation of Microtitre Plate 96-well microtitre plates are prepared by incubating each well with 100 μl of antisera (titre =5.0 mg/ml) to goat anti-bovine $IgG_2$ diluted 1:2 in carbonate buffer (0.015 M $Na_2CO_3$, 0.035 M $NaHCO_3$ and a pH of 9.6). Plates are incubated for 4 hours at 37° C. then the antisera solution is aspirated off and the plates washed by filling and emptying all wells 4 times with 0.05% v/v Tween 20 (polyoxyethylene sorbitan monolaurate) in phosphate buffered saline (PBS=0.010 M $Na_2HPO_4.2H_2$ 0, 0.003 M $KH_2PO_4$, 0.132 M NaCl and has a pH of 7.2). Plates are then sealed in foil bags.

Test Procedure

A substrate solution is prepared by adding 20 ml of CITrate buffer (0.05 M $Na_2HP0_4$, 0.024 M Citric acid monohydrate, 0.0035 M $H_2O_2$ at pH =5.0) to a vial containing 8mg o-phenylenediamine and mixing thoroughly. Standards for comparison are made by pipetting 100 μl of standard protein solutions of selected $IgG_2$ at concentrations of 0, 0.05, 0.1, 0.25 and 0.5 mg/ml in PBS into each of a number of wells.

Milk samples are taken by any suitable conventional method from cows to be tested and 100 μl of each milk sample is pipetted into the remaining wells. The plate is covered and incubated at 37° C. for 2 hours. The wells are then aspirated and washed 4 times with Tween 20/PBS as described above. 100 μof peroxidase-conjugated goat anti-bovine $IgG_2$ is pipetted into each well, and the plate is covered and incubated at 37° C. for 2 hours. Wells are aspirated and washed 4 times with Tween 20/PBS. 100 μl of substrate solution is added to each well. The microtitre plate is then covered, placed in the dark and allowed to incubate for 30 minutes at room temperature. The reaction is terminated by adding 50 μl 2.0M $H_2SO_4$ to each well. The absorbance of each well is read at 492 nm, a standard curve constructed from the wells containing standards, and the value of unknowns is determined from the standard curve.

An $IgG_2$ concentration in excess of 0.05 mg/ml is considered indicative of mastitis, and the mammal from which the sample was taken is classified as mastitis affected.

Example 3: Semi-quantitative Determination of $IgG_2$ in Bovine Milk Quarter Samples by Dot Blots Test Procedure Tris buffered saline (TBS) 0.9% (w/v) NaCl 10 mM Tris—HCl of pH 7.6, containing 0.05% (v/v) Tween 20) is required. CITrate buffer (0.05 M $Na_2HPO_4$, 0.024 M Citric acid monohydrate to a pH of 5.0) is also required. A substrate solution is also required; this is prepared by adding the CITrate buffer (containing 0.0035 M $H_2O_2$) to a vial containing 8 mg o-phenylenediamine and mixing thoroughly.

1 μl aliquots of bovine $IgG_2$ standard solution and goat anti-Bovine $IgG_2$ are dotted onto nitrocellulose. The dots are dried then incubated in a gelatine/TBS/Tween 20 (1% w/v) gelatin, solution for 4 hours to block out non-specific binding sites and dried again. 10 μl of each milk sample to be tested is serially diluted 2-fold with TBS then 1 μl applied to the antibody-containing dots. The dots are then soaked in 20 μl of the enzyme conjugate (goat anti-Bovine $IgG_2$), washed three times for 5 minutes each time in CITrate buffer. Substrate solution is then poured onto the nitrocellulose strip and the reaction is terminated after 5 minutes by washing the strips with distilled water.

Quantitation

Quantitation is achieved by determining at what dilution the $IgG_2$ becomes undetectable. Samples of milk are taken by any suitable conventional method from cows to be tested. By comparing the milk samples with the standard provided it is possible to make sample comparisons.

| | EXAMPLE DILUTION | | | | | | | |
|---|---|---|---|---|---|---|---|---|
| | 1:2 | 1:4 | 1:8 | 1:16 | 1:32 | 1:64 | 1:128 | 1:256 |
| Std: 1.0 mg/ml | 0 | 0 | 0 | 0 | 0 | 0 | 0 | + |
| Sample 1 | 0 | 0 | 0 | 0 | + | + | + | + |
| Sample 2 | 0 | 0 | + | + | + | + | + | + |

This example shows that the assay can detect $IgG_2$ to between 1/128 and 1/256 mg/ml, i.e.: 0.0078 and 0.0039 mg/ml.

Sample 1 contains at least 0.125 mg/ml (0.00078×16).

Sample 2 contains at least 0.031 mg/ml (0.0078×4).

If the sample is found to contain in excess of 0.05 mg $IgG_2$/ml milk, the mammal from which the sample is taken is classified as mastitis affected.

For finer resolution of affected quarters, it may be preferable to take separate samples from each mammary gland—or quarter in the case of cows—and regard any sample which significantly exceeds the minimum for that animal as indicative of an infection.

Example 4: Determination of $IgG_2$ in Bovine Milk Quarter Samples or Bulk Milk by Enzyme Linked Immuno-Sorbent Assay (ELISA)

Preparation of Microtitre Plates

Phosphate Buffered Saline (PBS) is required; 7.7 g/l NaCl, 1.48 g/l $Na_2$ $HPO_4$ anhydrous, 0.43 g/l $KH_2PO_4$ anhydrous to pH 7.2. Coat 96-well microtitre plates by incubating each well with 100 μl of affinity-purified goat anti-bovine $IgG_2$, 5 μg/ml in 0.5 M Carbonate/Bicarbonate buffer to a pH of 9.6. Plates are incubated overnight at room temperature, then the antisera solution is discarded and each well in the plate is filled with 1% Gelatin in 0.1 M Carbonate/Bicarbonate buffer (pH =9.6). The plates are incubated for 1 hour at room temperature, then the gelatin solution is discarded and the wells filled with 1% Glycine in Phosphate Buffered Saline (PBS), (7.7 g/l NaCl, 1.48 g/l $Na_2$ $HPO_{04}$ anhydrous, 0.43 g/l $KH_2PO_4$ anhydrous to pH =7.2). Plates are incubated for 1 hour at room temperature. The glycine solution is discarded and the plates are washed by filling and emptying all wells twice with 0.05% v/v Tween 20 in PBS (Wash Solution). Excess moisture around the plates is removed by blotting with absorbent paper and the plate is placed in a foil bag containing a desiccant sachet and sealed. Plates are refrigerated until required.

Test Procedure

Dilute positive control (0.1 mg/ml bovine $IgG_2$) and milk samples 1 in 2000 in 0.05% v/v Tween 20, 0.1% Gelatin in PBS (Sample Diluent Buffer SDB). 100 μl of SDB is pipetted into the first well, 100 μl diluted positive control into the second well and 100 μl diluted milk samples into the remaining wells in a row. The plate is covered and incubated at 37° C. for 1 hour. Discard the standards and milk samples and wash 4 times with Wash Solution. 100 μl of alkaline phosphatase-conjugated goat anti-bovine $IgG_2$ (conjugate) is pipetted into each well, and then the plate is covered and incubated at 37° C. for 1 hour.

N.B. Conjugate is diluted in SDB to give an absorbance of approximately 1.0 for the positive control. Wells are emptied and washed 4 times with Wash Solution. 100 μl of substrate solution is added to each well. Substrate solution is prepared by dissolving 0.02g of p-Nitrophenyl phosphate in 20 ml of diethanolamine buffer pH 9.8 (97 ml diethanolamine, 0.2 g sodium azide, 12 ml concentrated HCl per litre). Incubate at room temperature for 30 minutes then stop the reaction by the addition of 100 μl of 2 M NaOH to each well. The absorbance of each well is read at 405 nm, a standard curve constructed and the value of the unknown determined from the standard curve. An $IgG_2$ concentration in excess of 0.05 mg/ml is considered indicative of mastitis.

Thus it can be seen that the invention, at least in its preferred form, provides a powerful diagnostic test which is readily carried out by those skilled in the art, and which can be used to detect mastitis, including sub-clinical mastitis and mastitis caused by "minor pathogens". Thus dairy mammals, especially dairy cows, which are affected by mastitis may be readily identified for separation and treatment if required, and conversely healthy animals are readily identified by the test. Kits for performing the test may be readily produced and used, and the surprisingly simple basic principle and accuracy of the test can make it economically very advantageous.

Finally, it will be appreciated that various alterations or modifications may be made to the foregoing without departing from the scope of this invention.

we claim:

1. A method of testing for the existence of mastitis or subclinical mastitis in mammals, comprising the steps of:
   (a) obtaining a sample of milk from at least one mammal to be tested,
   (b) measuring the level of immunoglobulin ($IgG_2$) in said sample of milk,
   (c) determining the level of $IgG_2$ present per milliliter of milk,
   (d) comparing the level of $IgG_2$ determined in step (c) with a reference at about 0.05 mg $IgG_2$ per milliliter of milk,
   (e) classifying said mammal or group of mammals as mastitis affected if said $IgG_2$ is present in said sample of milk at or above the level of the reference.

2. A method as claimed in claim 1, wherein the step of determining the level of $IgG_2$ is carried out by the method of Enzyme Linked Immuno-Sorbent Assay (ELISA) comparison with immunoglobulin solutions of known concentration, comprising measurement of the intensity of a color formed within a substrate as a result of enzymic activity by enzymes which are caused to become attached to the specific antibody-immunoglobulin $IgG_2$ complex.

* * * * *

UNITED STATES PATENT AND TRADEMARK OFFICE
CERTIFICATE OF CORRECTION

PATENT NO. : 5,807,684
DATED : September 15, 1998
INVENTOR(S) : Maxine Helen SIMMONS et al.

It is certified that error appears in the above-indentified patent and that said Letters Patent is hereby corrected as shown below:

On the title page, Item [22], change "Jan. 24, 1994" to --January 21, 1994--.

Signed and Sealed this

Twenty-third Day of March, 1999

Attest:

Q. TODD DICKINSON

Attesting Officer

Acting Commissioner of Patents and Trademarks